United States Patent
Thompson et al.

[19]

[11] Patent Number: 5,931,844
[45] Date of Patent: Aug. 3, 1999

[54] SURGICAL DRIVE TOOL

[75] Inventors: Kenneth K. Thompson, Palm Harbor; Randall D. Ross, Largo, both of Fla.; Steven W. Ek, Bolton, Mass.

[73] Assignee: Smith & Nephew, Inc., Memphis, Tenn.

[21] Appl. No.: 09/052,651

[22] Filed: Mar. 31, 1998

[51] Int. Cl.⁶ ..................................................... A61B 17/00
[52] U.S. Cl. ........................... 606/144; 606/139; 606/232
[58] Field of Search ..................................... 606/232, 139, 606/144, 148, 73, 74, 75, 181, 182, 145

[56] References Cited

U.S. PATENT DOCUMENTS

| | | |
|---|---|---|
| 2,665,597 | 1/1954 | Hill . |
| 3,541,591 | 11/1970 | Hoegerman . |
| 3,664,345 | 5/1972 | Dabbs et al. . |
| 3,845,772 | 11/1974 | Smith . |
| 3,910,281 | 10/1975 | Kletschka et al. . |
| 3,976,079 | 8/1976 | Samuels et al. . |
| 4,235,238 | 11/1980 | Ogiu et al. . |
| 4,287,807 | 9/1981 | Pacharis et al. . |
| 4,291,698 | 9/1981 | Fuchs et al. . |
| 4,532,926 | 8/1985 | O'Holla . |
| 4,573,844 | 3/1986 | Smith . |
| 4,669,473 | 6/1987 | Richards et al. . |
| 4,741,330 | 5/1988 | Hayhurst . |
| 4,744,353 | 5/1988 | McFarland . |
| 4,744,793 | 5/1988 | Parr et al. . |
| 4,750,492 | 6/1988 | Jacobs . |
| 5,078,731 | 1/1992 | Hayhurst . |
| 5,224,946 | 7/1993 | Hayhurst . |
| 5,268,001 | 12/1993 | Nicholson et al. . |
| 5,324,308 | 6/1994 | Pierce . |
| 5,423,860 | 6/1995 | Lizardi et al. . |
| 5,458,601 | 10/1995 | Young et al. . |
| 5,464,427 | 11/1995 | Curtis et al. . |
| 5,480,403 | 1/1996 | Lee et al. . |
| 5,486,197 | 1/1996 | Le et al. . |
| 5,573,548 | 11/1996 | Nazre et al. . |
| 5,584,835 | 12/1996 | Greenfield . |
| 5,643,321 | 7/1997 | McDevitt . |
| 5,649,963 | 7/1997 | McDevitt . |

FOREIGN PATENT DOCUMENTS

| | | |
|---|---|---|
| 0 270 704 A1 | 6/1988 | European Pat. Off. . |
| 0 340 159 A1 | 3/1989 | European Pat. Off. . |
| 0 409 364 A2 | 1/1991 | European Pat. Off. . |
| 0 502 509 A1 | 9/1992 | European Pat. Off. . |
| 0 574 707 A1 | 12/1993 | European Pat. Off. . |
| 0 591 991 A2 | 4/1994 | European Pat. Off. . |
| WO 95/32670 | 7/1995 | WIPO . |
| WO 95/29637 | 11/1995 | WIPO . |

OTHER PUBLICATIONS

Product Focus, ROC Fastener System, "ID Innovasive Devices, Inc.", 1994.

*Primary Examiner*—Michael Buiz
*Assistant Examiner*—Vikki Trinh
*Attorney, Agent, or Firm*—Fish & Richardson P.C.

[57] ABSTRACT

A handle assembly for a drive tool includes a plunger actuator configured to move a plunger of the drive tool between a retracted position and an extended position, an outer tube actuator configured to move an outer tube of the drive tool between a retracted position and an extended position, and a coupler configured to move the outer tube from its extended position to its retracted position in response to movement of the plunger from its extended position to its retracted position. The drive tool delivers a suture securing device to a surgical site. When the plunger actuator moves the plunger to its extended position, a second member of the device is secured to a first member of the device. When the plunger actuator moves the plunger to a second, further extended position, the plunger deploys the secured first and second members from the drive tool.

20 Claims, 8 Drawing Sheets

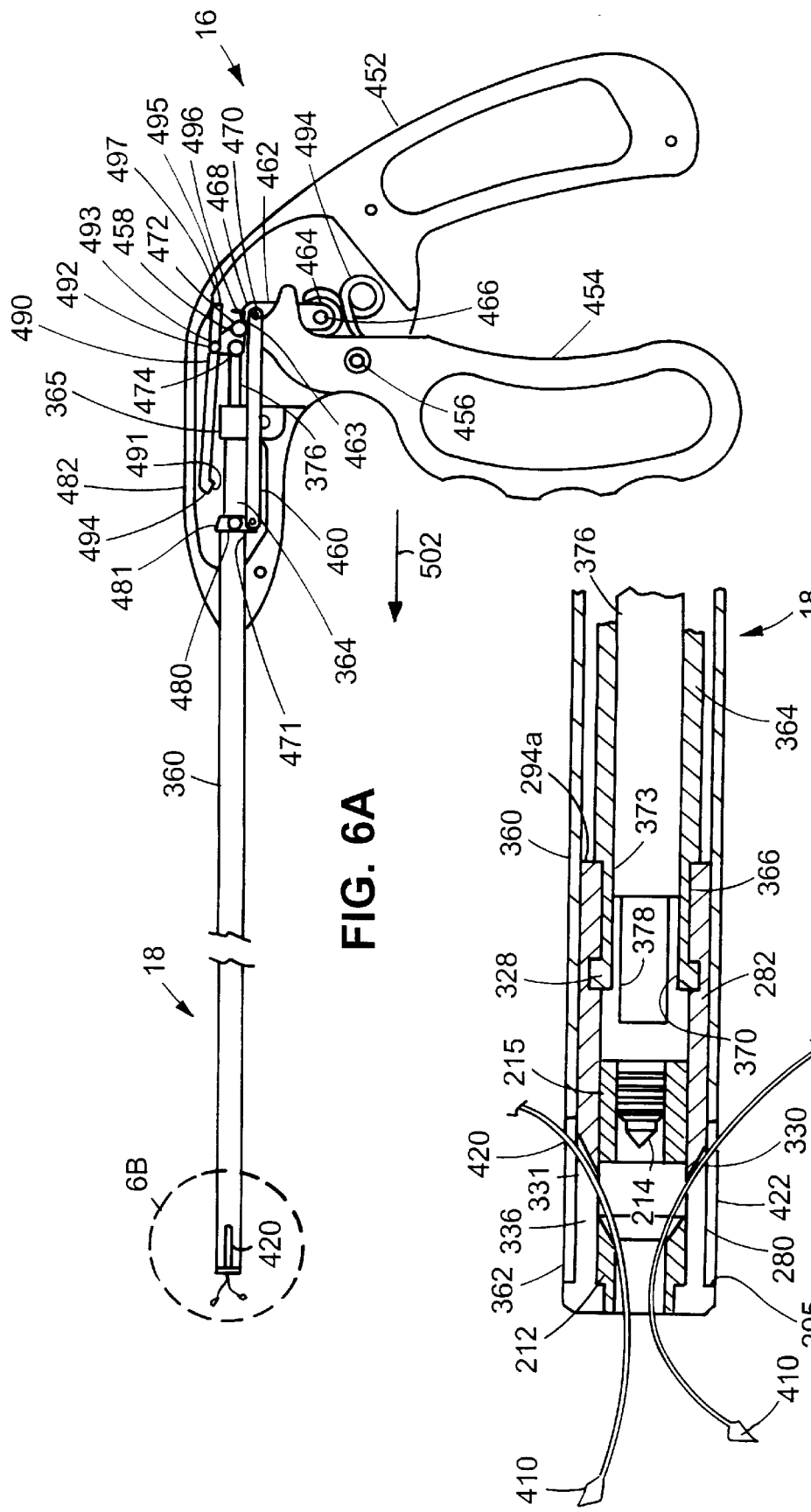

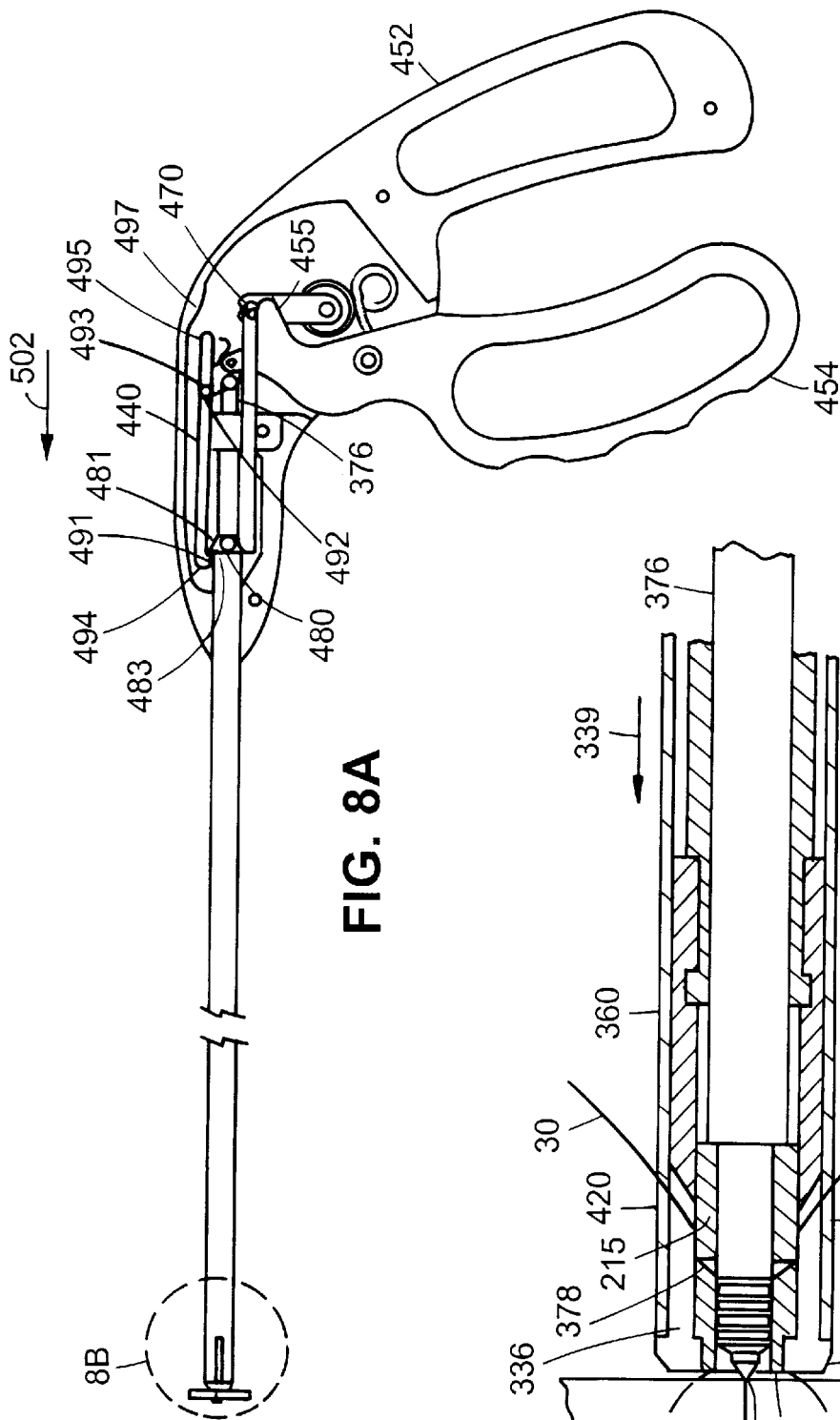

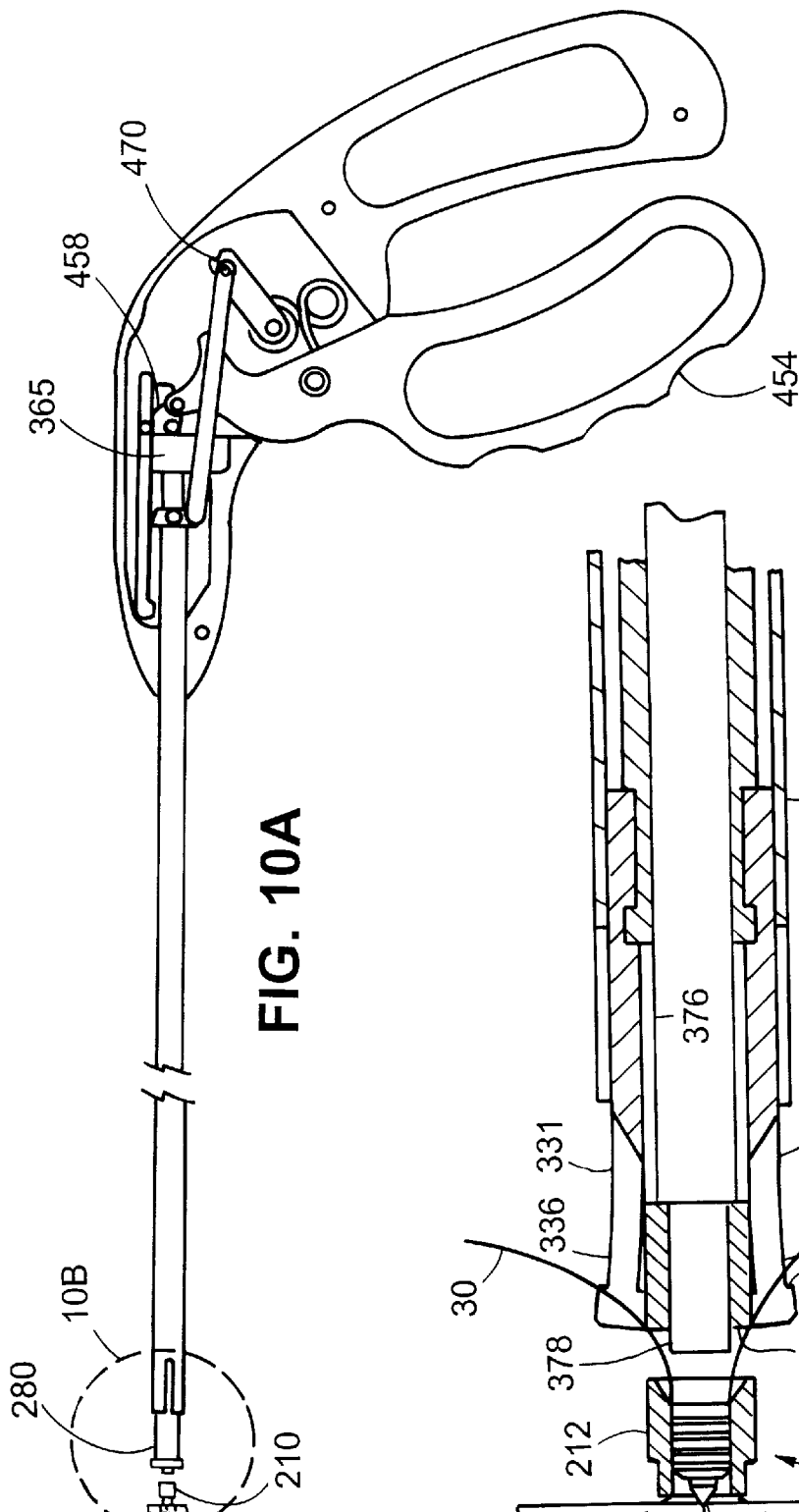

SURGICAL DRIVE TOOL

BACKGROUND OF THE INVENTION

This invention relates to a surgical drive tool.

A common type of surgical drive tool for deploying a surgical device includes a stationary handle and a movable trigger. An outer tube in which the surgical device is housed is typically attached to the stationary handle. An actuator rod located within the outer tube ad axially movable relative to the outer tube is typically attached to the trigger. The user pulls on the trigger to advance the rod deploying the surgical device form the outer tube.

SUMMARY OF THE INVENTION

According to one aspect of the invention, a handle assembly for a drive tool includes a plunger actuator configured to move a plunger of the drive tool between a retracted position and an extended position, an outer tube actuator configured to move an outer tube of the drive tool between a retracted position and an extended position, and a coupler configured to move the outer tube from its extended position to its retracted position in response to movement of the plunger from its extended position to its retracted position.

Preferred embodiments may include one or more of the following features.

The plunger actuator is configured to move the plunger to a second, further extended position. A stop member of the handle assembly has a first position limiting the plunger actuator from moving the plunger toward its second, extended position, and a second position permitting the plunger actuator to move the plunger to its second, extended position.

Preferably, the outer tube actuator includes a user engageable member for moving the outer tube to a second, further retracted position.

The coupler is mounted to the plunger actuator and engages the outer tube actuator when the outer tube is in its extended position and the plunger is in its extended position.

A biasing member biases the plunger actuator to move the plunger toward its retracted position. A holding member holds the outer tube actuator stationary to selectively maintain the outer tube in its extended position.

In embodiments of the invention, the plunger actuator is a trigger handle pivotably mounted to a stationary handle. The outer tube actuator is a slide member mounted to the outer tube.

An intermediate tube of the drive tool is located between the outer tube and the plunger and the handle assembly has a support to which the intermediate tube is mounted. The support limits movement of the plunger beyond its second, extended position.

According to another aspect of the invention, a handle assembly for a drive tool includes a stationary handle, a trigger handle pivotably mounted to the stationary handle, a slide member, a coupler, and a stop member. The trigger handle is connected to the plunger to move the plunger between a retracted position, a first extended position, and a second, further extended position. The slide member is mounted to the outer tube to move the outer tube between an extended position, a first retracted position, and a second, further retracted position. The slide member has a user engageable member for moving the outer tube to its second, further retracted position. The coupler is connected to the trigger handle and engages the slide member when the outer tube is in its extended position and the plunger is in its extended position. The coupler moves the outer tube from its extended position to its first retracted position in response to movement of the plunger from its first extended position to its retracted position. The stop member has a first position limiting the trigger handle from moving the plunger toward its second, extended position, and a second position permitting the trigger handle to move the plunger to its second, extended position.

According to another aspect of the invention, a drive tool assembly is configured to deliver a suture securing device to a surgical site. The suture securing device includes a first member and a second member configured for secure engagement with the first member. The drive tool includes the outer tube, the plunger, the plunger actuator, the outer tube actuator, and the coupler. The first and second members are located within the outer tube. When the plunger actuator moves the plunger to its extended position, the second member is moved into secure engagement with the first member.

Preferred embodiments may include one or more of the following features.

The plunger actuator is configured to move the plunger to a second, further extended position. In this position, the plunger deploys the secured first and second members from the drive tool assembly.

The suture securing device includes a cartridge containing the first and second members, and the drive tool assembly includes an intermediate tube located between the outer tube and the plunger for securing the cartridge to the drive tool.

Preferably, the outer tube actuator is configured to move the outer tube to a second, further retracted position. The intermediate tube is configured to engage and disengage the cartridge when the outer tube is in its second, further retracted position.

Another aspect of the invention features a method of delivering a surgical device having a first member and a second member includes providing a drive tool assembly including an outer tube, a plunger located within the outer tube, a plunger actuator configured to move the plunger, and a coupler coupling the plunger and the outer tube. The method further includes moving the plunger actuator to partially advance the plunger to move one of the members into secure engagement with the other member. Movement of the plunger actuator causes the coupler to engage the outer tube. The plunger actuator is released to move the plunger proximally. The coupler and the outer tube engaged by the coupler move proximally in response to the proximal motion of the plunger.

Preferred embodiment of this aspect of the invention may include one or more of the following features.

The plunger actuator is moved a second time to fully advance the plunger to eject the surgical device from the drive tool assembly. An outer tube actuator is moved to move the outer tube further proximally.

Among other advantages, the drive tool provides a simple way of loading, manipulating and deploying a surgical device. The coupler automates the motion of the outer sheath from its fully extended position to its partially retracted position. This eliminates the need for the user to set the desired partially retracted position of the outer sheath. The holding member prevents inadvertent retraction of the outer tube form its extended position during advancement of the drive tool to the surgical site.

Other features and advantages of the invention will be apparent from the following detailed description, and from the claims.

BRIEF DESCRIPTION OF THE DRAWINGS

FIG. 6A is a partially cut-away view of the drive tool of FIG. 1;

FIG. 6B is an enlarged, cross-sectional view of region 6B of FIG. 6A, rotated 90° with respect to FIG. 6A;

FIG. 8A is a partially cut-away view of the drive tool of FIG. 1 shown in a pin advancing position;

FIG. 8B is an enlarged, cross-sectional view of region 8B of FIG. 8A;

FIG. 10A is a partially cut-away view of the drive tool of FIG. 1 shown in a suture collet deploying position; and FIG. 10B is an enlarged, cross-sectional view of region 10B of FIG. 10A.

DESCRIPTION OF THE PREFERRED EMBODIMENT

Figure 1:
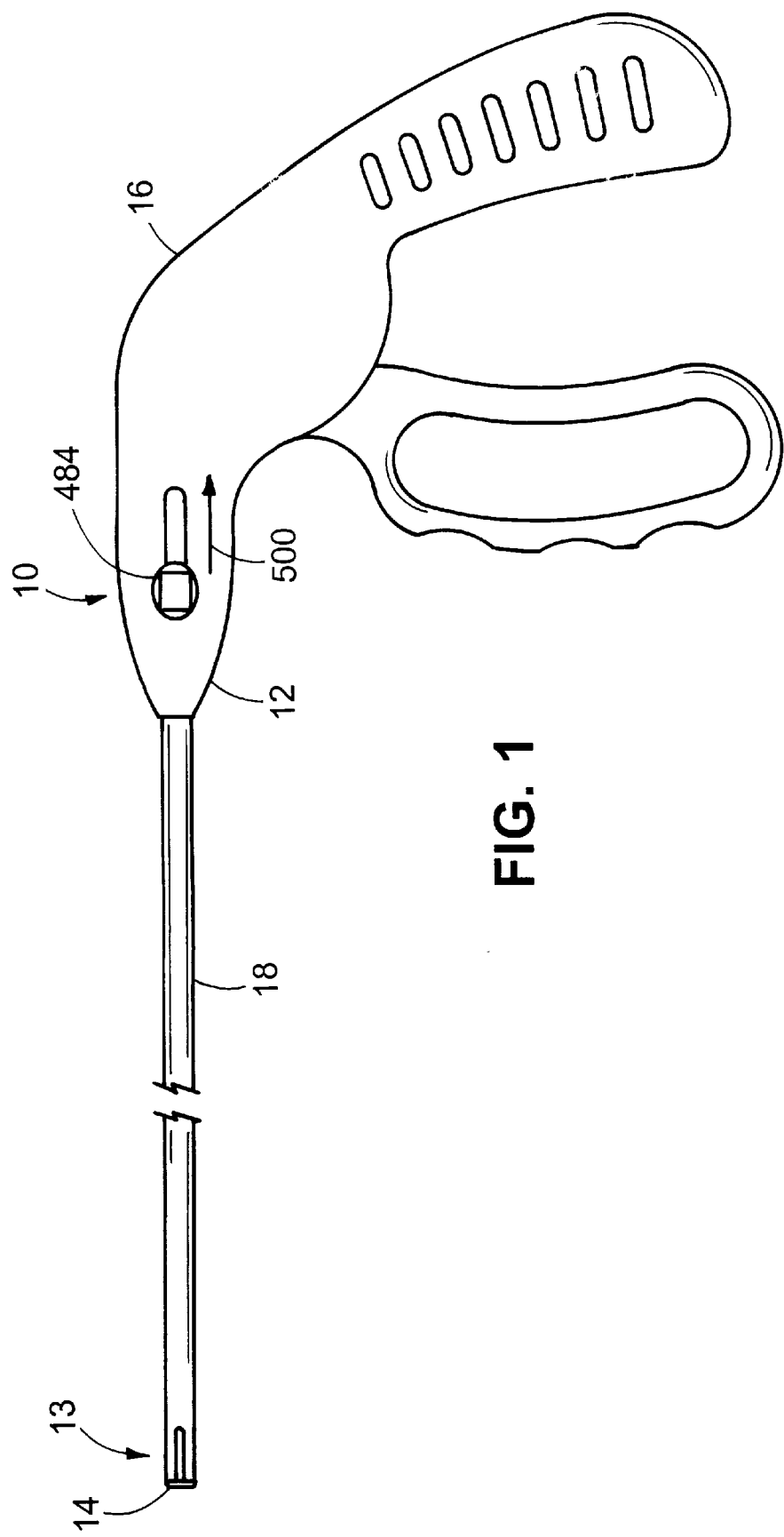
FIG. 1 shows a drive tool according to the invention.

Referring to FIG. 1, a suture securing apparatus 10 includes a drive tool 12 and a suture collet assembly 14 housed within a distal end 13 of drive tool 12. Drive tool 12 includes a handle assembly 16 and a tube assembly 18. The drive tool is used to emplace a suture collet 210 (FIG. 10B) of suture collet assembly 14 in the body. Suture collet 210 replaces conventional securing techniques (e.g., knot tying) for securing a suture in place, as described, e.g., in Ek, U.S. Ser. No. 08/915,758, filed Aug. 21, 1997, titled SUTURING TISSUE, Ek et al., U.S. Ser. No. 08/783,126, filed Jan. 14, 1997, titled SUTURE COLLET, and Ek et al., U.S. Ser. No. 08/605,767, filed Feb. 22, 1996, titled SUTURE COLLET, all hereby incorporated herein by reference.

Figure 2:
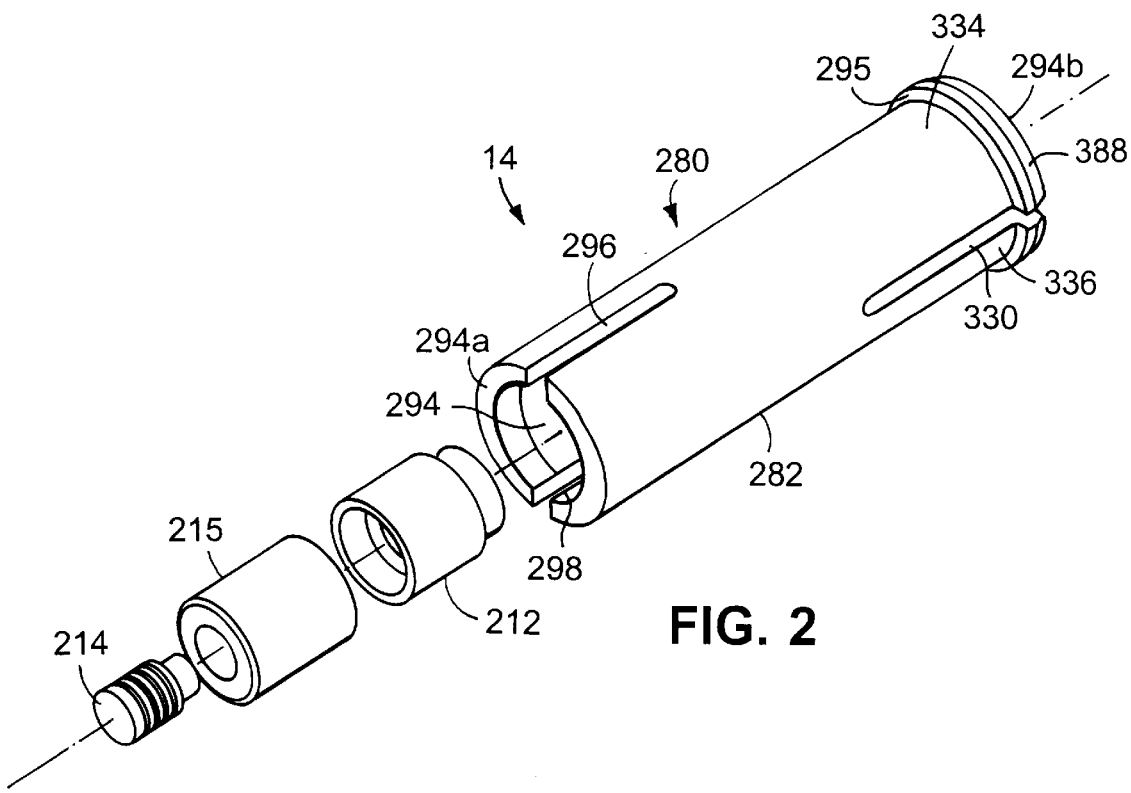
FIG. 2 is an exploded perspective view of a suture collet assembly which can be deployed with the drive tool of FIG. 1.

Referring to FIG. 2, in which a representative embodiment of a suture collet assembly is shown, suture collet assembly 14 includes a cartridge 280 for carrying suture collet 210. Suture collet 210 includes an outer locking ring 212 and an inner locking pin 214 which securely fasten a suture in place within a bore 216 in ring 212 when pin 214 is inserted into bore 216. Cartridge 280 couples to drive tool 12, described below, which inserts pin 214 into ring 212.

Figure 3:
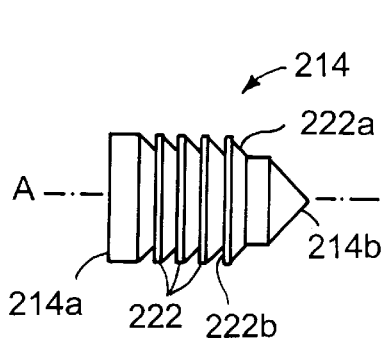
FIG. 3 is a cross-sectional view of an inner member of the suture collet assembly of FIG. 2.

Referring to FIG. 3, bore 216 is axially-oriented and cylindrical. A portion of the interior surface of ring 212 which defines bore 216 is threaded 236. Bore 216 extends completely through ring 212, from proximal end 212a to distal end 212b, along a longitudinal central axis 244 of ring 212. Bore 216 is tapered 216a from a larger diameter at proximal end 212a to a smaller diameter where threads 236 begin at 216b. Ring 212 has an outer diameter, $D_1$, of 0.123 inches over the majority 236a of its length, and a smaller outer diameter, $D_2$, of 0.105 inches over the remainder 236b of it length. A circumferential ledge 220 is located at the junction of diameters $D_1$ and $D_2$.

Figure 4:
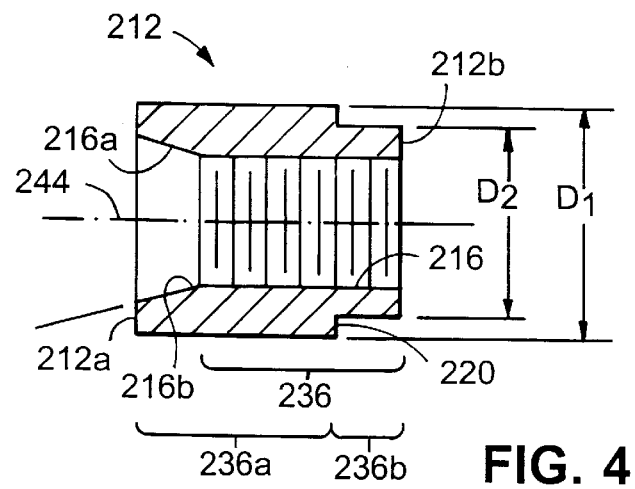
FIG. 4 is a side view of an outer member of the suture collet assembly of FIG. 2.

Referring to FIG. 4, pin 214 is generally cylindrical in shape and is sized to enter bore 216. A portion of the exterior surface of pin 214 includes a series of axially spaced ridges 222 for lockingly engaging ring threads 236 in a ratchet-like manner when pin 214 is progressively inserted into bore 216 thus securing pin 214 in any one of a plurality of locked positions in ring 212 to secure suture between ring 212 and pin 214 within bore 216.

The circumferentially oriented ridges 222 of pin 214 are axially spaced along pin 214 between proximal end 214a and distal end 214b. The leading (distal) surfaces 222a of ridges 222 are inclined (e.g., at 45 degrees) relative to a longitudinal axis A of pin 214 to slide past threads 236 of ring 212 during insertion, and the trailing (proximal) surfaces 222b of ridges 222 are oriented perpendicular to long axis A to lockingly engaging threads 236 when pin 214 has been inserted by the desired amount. Distal end 214b of pin 214 is conically shaped to help guide pin 214 into bore 216.

The overall size of suture collet 210 with pin 214 inserted into ring 212 corresponds approximately to the size of three successive throws of a suture knot. For example, ring 212 is 0.15 inches long and has a maximum outer diameter of 0.125 inches; pin 214 is only 0.095 inches long (and thus can fit lengthwise entirely within ring 212) and has a maximum outer diameter of 0.068 inches. Ring 212 and pin 214 can be made from a non-absorbable material such as polyacetal available from M. Holland Co., Northbrook, Ill., or a bio-absorbable material, such as Maxon, a polyglyconate, available from Davis & Geck.

Figure 5:
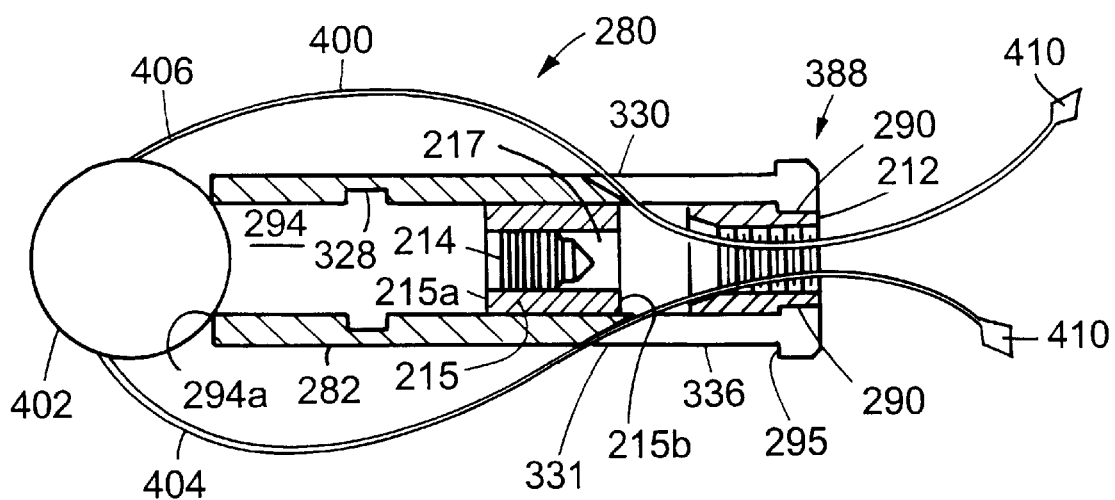
FIG. 5 is a cross-sectional view of the suture collet assembly of FIG. 2.

Referring to FIGS. 2 and 5, cartridge 280 includes a hollow sleeve 282 with an axial passage 294 extending completely through sleeve 282, from proximal end 294a to distal end 294b. The distal end 294b of sleeve 282 is provided with a pair of axial slots 330, 331 which define a pair of resilient arms 334, 336 which form a clamp 388 to hold suture collet ring 212 in place therebetween. Interior lips 290 on arms 334, 336 form a close fit against the smaller diameter region 236b of ring 212.

Sleeve 282 has proximal slots 296, 298, and a circumferential groove 328 in inner wall 282a of sleeve 282 for purposes to be described. A distal end of arms 334, 336 has an enlarged outer diameter relative to that of the remainder of sleeve 282, such that a shoulder 295 is defined, also for purposes to be discussed.

Pin 214 is supported within passage 294 by a carrier 215. Pin 214 is located within an opening 217 in carrier 215 extending from a proximal end 215a of carrier 215 to a distal end 215b. Carrier 215 acts to center pin 214 within cartridge passage 294.

A suture threader 400 is used to thread suture through ring 212 during operation. A proximal cap 402 is connected to the proximal ends of a pair of suture threader wires 404, 406 which respectively pass through slots 330, 331 and into passage 294. The free ends of wires 404, 406 pass through bore 216 of suture collet ring 212. Wires 404, 406 terminate in threading loops 410. Alternatively, wire 404 terminates in suture, as described in Ek, SUTURING TISSUE, supra.

To assemble the cartridge assembly of FIG. 5, ring 212 is first placed within passage 294 and slid forward so that ledge 220 engages lip 290. Wires 404, 406 of suture threader 400 are passed through slots 330, 331 and through ring bore 216. Pin 214 is then placed within carrier 215 and carrier 215 with pin 214 are together placed within passage 294 and positioned just proximally of ring 212.

To position suture collet 210 at a surgical site, the cartridge assembly is secured to drive tool 12, the drive tool is advanced to the surgical site, and the user manipulates the drive tool to deploy the suture collet from the cartridge assembly.

Referring to FIG. 6B, tube assembly 18 of drive tool 12 has an outer sheath 360 which fits over sleeve 282 of the cartridge assembly. A distal end 362 of outer sheath 360 engages shoulder 295 of sleeve 282. Outer sheath 360 includes axial slots 420, 422 aligned with slots 330, 331 for passage of suture 30. A grasper 364 located within sheath 360 has a circumferential groove 366 with a distal ridge 370 configured to fit within groove 328 of sleeve 282, and a shoulder 373 which engages proximal end 294a of sleeve 282 to secure cartridge 280 within drive tool 12.

A plunger 376 is slidable within grasper 364 and has a smaller diameter extension 378 which fits within carrier 215 to engage pin 214 and progressively insert pin 214 into passage 216 of ring 212. Carrier 215 acts to center pin 214 such that plunger 376 squarely engages pin 214.

Plunger 376 and outer sheath 360 are moved by manipulating handle assembly 16 of drive tool 12. Referring to FIG. 6A, handle assembly 16 includes an actuating trigger 454 pivotably mounted about a pivot pin 456 to a stationary handle 452. Plunger 376 is mounted to trigger 454 by a mount 458 such that movement of trigger 454 controls the movement of plunger 376. A first pivot pin 472 attaches mount 458 to trigger 454 and a second pivot pin 474 attaches mount 458 to plunger 376.

Outer sheath 360 is attached to an actuating slide bar 460 of handle assembly 16. Slide bar 460 is mounted to handle 452 by a stop bar 462. A first end 464 of stop bar 462 is pivotably mounted to handle 452 by a pin 466. A second end 468 of stop bar 462 is pivotably mounted to slide bar 460 by a stop pin 470. Slide bar 460 is pivotably connected to a slide member 480 by a pin 471. Slide member 480 attaches the slide bar to outer sheath 360. Extending from member 480 through handle body 482 is a user actuated slide 484 (FIG. 1). Moving slide 484 axially causes corresponding axial movement of outer sheath 360 relative to handle assembly 16.

A coupling arm 490 functionally couples trigger 454 with slide bar 460. Coupling arm 490 is attached to mount 458 by a pivot pin 492. A spring 493 biases coupling arm 490 to pivot counterclockwise about pivot pin 492. Engagement of a back end 495 of coupling arm 490 against a boss 497 on handle body 482 overcomes the spring force to hold coupling arm 490 in the unlatched position shown in FIG. 6A. Coupling arm 490 and mount 480 of slide bar 460 include complementary ramps 491 and 481, respectively. A hook end 494 of coupling arm 490 can be moved into position to engage mount 480, as described below.

A trigger spring 494 biases trigger 454 toward a position spaced from handle 452 such that plunger 376 is in a retracted position as shown in FIG. 6B. A holding spring 496 engages a detent 463 in stop bar 462 to hold slide bar 460, and thus outer sheath 360, in an extended position as shown in FIG. 6A. Grasper 364 is held in a fixed position relative to plunger 376 and outer sheath 360 by mounting of grasper 364 to handle assembly 16 with a support 365 extending form handle body 482.

Figure 7A:
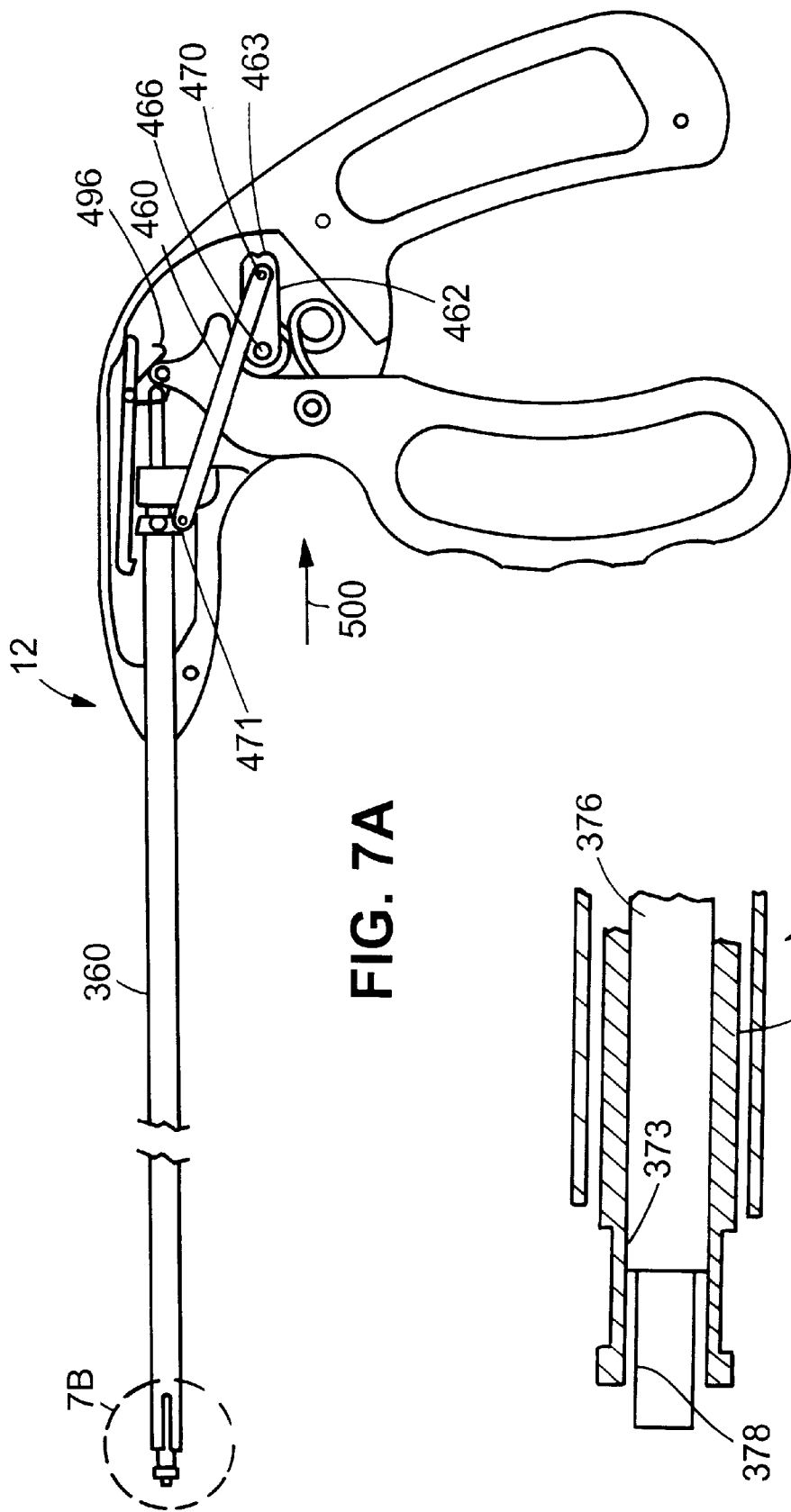
FIG. 7A is a partially cut-away view of the drive tool of FIG. 1 shown in a cartridge loading position.
Figure 7B:
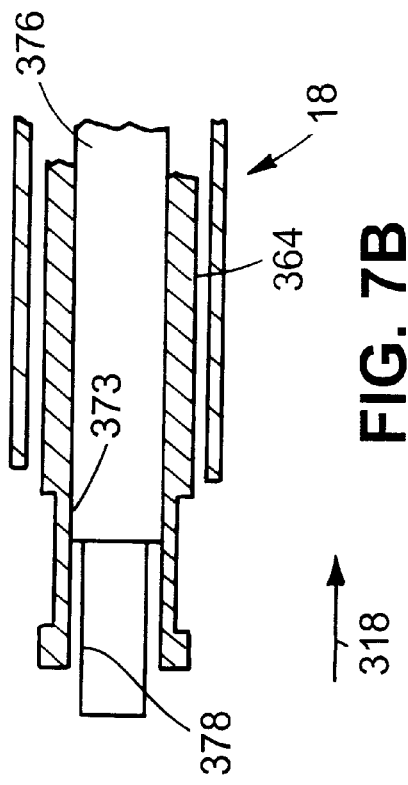
FIG. 7B is an enlarged, cross-sectional view of region 7B of FIG. 7A.

Referring to FIGS. 7A and 7B, to load cartridge 280 into insertion tool 12, the user moves slide 484 proximally in the direction of arrow 500 (see FIG. 1) to fully retract outer tube 360 to a cartridge loading position. This proximal movement of slide 484 causes stop bar 462 to pivot about pin 466 and slide arm 460 to pivot about pins 470 and 471. With the outer tube fully retracted and grasper groove 366 exposed, cartridge 280, with ring 212, pin 214, carrier 215, and suture threader 400 preinstalled as described above and cap 402 moved aside to expose passage 294, is inserted onto grasper 364 until distal ridge 370 reaches and snap fits within sleeve groove 328. Proximal slots 296, 298 in sleeve 282 permit proximal end 294a of sleeve 282 to widen during insertion of grasper 364.

Referring again to FIGS. 6 and 6B, the user then moves slide 484 distally (in the direction of arrow 502) to fully extend outer tube 360 over cartridge 280 to capture the cartridge within insertion tool 12. Note that in the configuration shown, sheath 360 envelopes all but the distal ends of clamping arms 334, 336, thereby holding them securely in place against suture collet ring 212. Holding spring 496 engages detent 463 of stop bar 462 to hold outer sheath 360 in its extended position. Drive tool 12 is now ready to install suture collet 210 in the body.

Suture collet 210 is emplaced in the body with cartridge 280 and drive tool 12 as follows. Suture threader 400 is moved proximally (arrow 318) using cap 402 to pull suture 30 through suture collet ring 212, slots 330, 331 and slots 420, 422. Drive tool 12 is then advanced, for example, through a conventional cannula used in arthroscopic or laproscopic surgery, to the fixation site. Insertion tool 12 is maneuvered at the surgical site to position suture collet ring 212 as desired, e.g., against the upper surface of a vessel 2 (FIG. 8B).

Referring to FIGS. 8A and 8B, pulling trigger 454 toward handle 452 causes plunger 376 and coupling arm 490 to move distally (in the direction of arrow 502). As shown in FIG. 8B, plunger 376 acts to initially slide carrier 215 with pin 214 distally. When carrier 215 contacts ring 212, carrier 215 stops while plunger extension 378 continues to move distally, thereby progressively inserting pin 214 axially into bore 216 of ring 212. With sheath 360 in its distal firing position, sheath 360 holds cartridge 280 securely in place while pin 214 is being inserted preventing the cartridge, pin, and ring from exiting the drive tool. Pin 214 is inserted into bore 216 of ring 212 securing suture 30 between ring 212 and pin 214. The distal extension of plunger 376, and thus the amount pin 214 is inserted into ring 212, is determined by contact of a nose 455 of trigger 454 against stop pin 470 which prevents further distal extension of the plunger.

The distal movement of coupling arm 490 caused by pulling trigger 454 acts to release arm end 495 from boss 497. Spring 493 causes arm 490 to rotate counterclockwise about pin 492. As arm 490 moves distally, arm ramp 491 rides over mount ramp 481 with hook 494 engaging distal end 483 of mount 480.

Figure 9A:
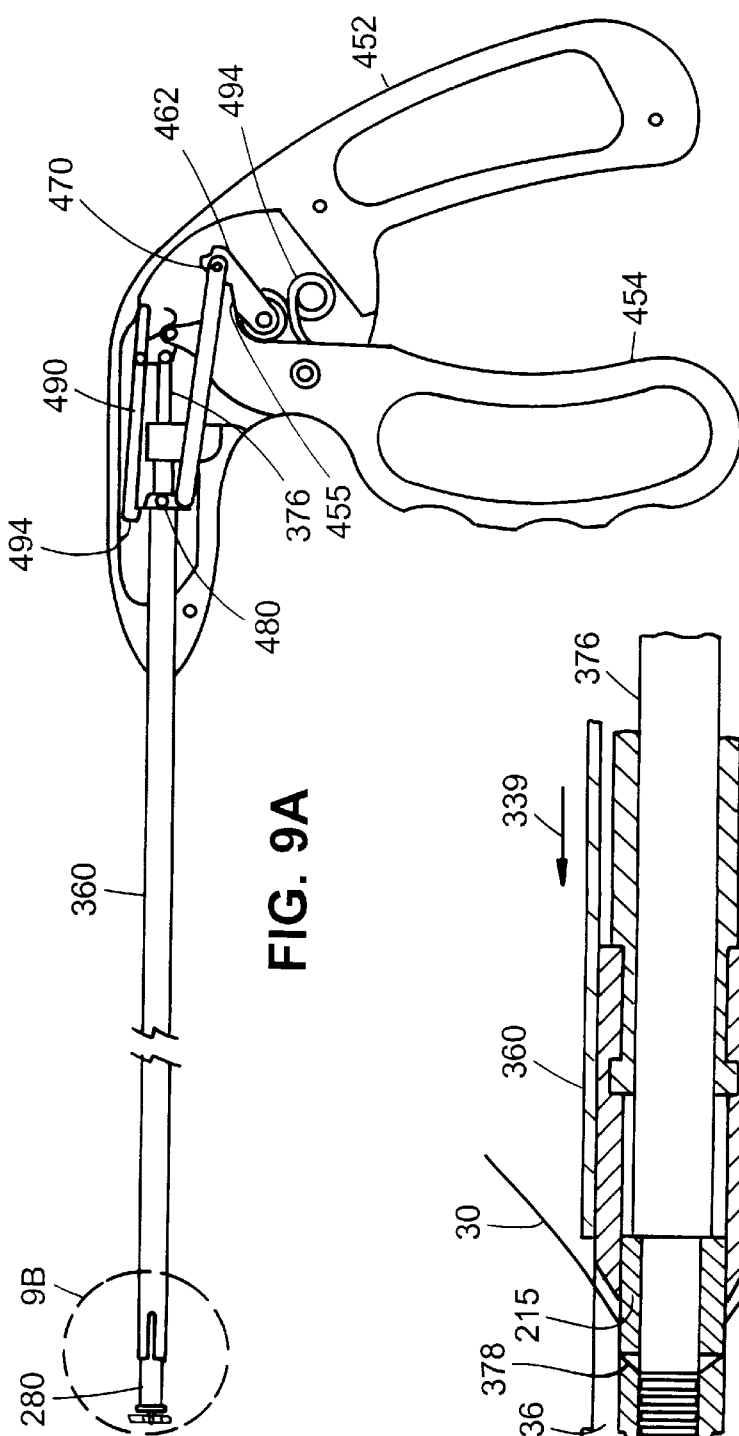
FIG. 9A is a partially cut-away view of the drive tool of FIG. 1 shown in an outer sheath retracting position.
Figure 9B:
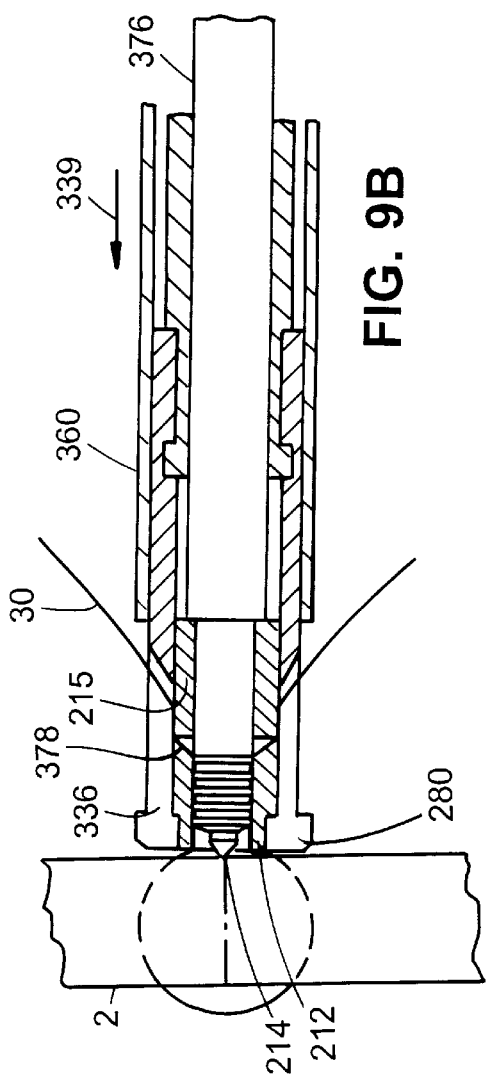
FIG. 9B is an enlarged, cross-sectional view of region 9B of FIG. 9A.

Referring to FIGS. 9A and 9B, when the user releases trigger 454, spring 494 causes the trigger to move away from handle 452. This movement of trigger 454 causes plunger 376 and coupling arm 490 to be retracted and bar 462 to be rotated such that pin 470 is moved out of engagement with nose 455 of trigger 454. Since mount 480 connected to outer sheath 360 is engaged by hook 494 of coupling arm 490, retraction of coupling arm 490 causes outer sheath 360 to be partially retracted as shown in FIG. 9B to a collet release position. The partially retracted position of sheath 360 prevent cartridge 280 from disengaging from grasper 364 while permitting cartridge arms 334, 336 to flex outward to allow the suture collet to be expelled from the cartridge.

Referring to FIGS. 10A and 10B, with stop pin 470 held out of the way by friction, the user can pull trigger 454 closer to handle 452 such that plunger 376 is fully extended distally to deploy collet 210 from cartridge 280. With sheath 360 partially retracted, arms 334, 336 of cartridge 280 flex outwardly as suture collet 210 is moved distally thereby permitting extension 378 to push suture collet 210 distally from cartridge 280. The distance that plunger 376 can be moved distally is limited by engagement of mount 458 with plunger support 365 which limits the rotation of trigger 454, such that carrier 215 is not also pushed from cartridge 280. Suture 30 is released from cartridge 280 by passage of suture 30 through slots 330, 331.

To remove cartridge 280 from insertion tool 12, the user moves slide 484 fully proximally (as in FIGS. 7A and 7B) and removes the cartridge from grasper 364.

Other embodiments are within the scope of the following claims.

For example, plunger 84 and pin 14 can be manufactured as one unit. After the pin is inserted into the ring, rotation of plunger 84 would dislodge the pin from the plunger. Plunger 84 can include a distal cam surface such that rotation of the plunger acts to force arms 134, 136 apart to facilitate removal of the suture collet from cartridge 80.

Suture collet 210 can used wherever a suture knot would be tied, e.g., in ligating branches of vessels, in soft-tissue repair, in reducing tissues, and in securing tissue to bone.

Ring 12 and pin 14 and ring 212 and pin 214 can be connected in other ways. For example, in the ratcheting technique discussed herein, pin 214 may be threaded and ring 212 can include ridges 222. A single ridge 222 can be used in place of the axially spaced series of ridges discussed above. An inner pin can be positioned first and an outer ring can be driven over the inner pin.

Drive tool 12 is not limited to use with the particular surgical devices described.

What is claimed is:

1. A handle assembly for a drive tool, the drive tool including an outer tube and a plunger located within the outer tube, the handle comprising:

a plunger actuator configured to move the plunger between a retracted position and an extended position, an outer tube actuator configured to move the outer tube between a retracted position and an extended position, and a coupler coupling the plunger and the outer tube, the coupler being configured to move the outer tube from its extended position to its retracted position in response to movement of the plunger from its extended position to its retracted position.

2. The handle assembly of claim 1 wherein the plunger actuator is configured to move the plunger to a second, further extended position, the handle assembly further including a stop member having a first position limiting the plunger actuator from moving the plunger toward its second, extended position, and a second position permitting the plunger actuator to move the plunger to its second, extended position.

3. The handle assembly of claim 1 wherein the outer tube actuator is configured to move the outer tube to a second, further retracted position.

4. The handle assembly of claim 3 wherein the outer tube actuator includes a user engageable member for moving the outer tube to its second, further retracted position.

5. The handle assembly of claim 1 wherein the coupler is mounted to the plunger actuator, the coupler being configured to engage the outer tube actuator when the outer tube is in its extended position and the plunger is in its extended position.

6. The handle assembly of claim 1 further including a biasing member for biasing the plunger actuator to move the plunger toward its retracted position.

7. The handle assembly of claim 1 further including a holding member for holding the outer tube actuator stationary to selectively maintain the outer tube in its extended position.

8. The handle assembly of claim 1 wherein the plunger actuator comprises a trigger handle pivotably mounted to a stationary handle.

9. The handle assembly of claim 1 wherein the outer tube actuator comprises a slide member mounted to the outer tube.

10. The handle assembly of claim 1 wherein the drive tool further comprises an intermediate tube located between the outer tube and the plunger, the handle assembly further comprising a support to which the intermediate tube is mounted.

11. The handle assembly of claim 10 wherein the plunger actuator is configured to move the plunger to a second, further extended position, the support being arranged to limit movement of the plunger beyond its second, extended position.

12. A handle assembly for a drive tool, the drive tool including an outer tube and a plunger located within the outer tube, the handle comprising:

a stationary handle and a trigger handle pivotably mounted to the stationary handle, the trigger handle being connected to the plunger to move the plunger between a retracted position, a first extended position, and a second, further extended position, a slide member mounted to the outer tube to move the outer tube between an extended position, a first retracted position, and a second, further retracted position, the slide member including a user engageable member for moving the outer tube to its second, further retracted position, a coupler connected to the trigger handle, the coupler being configured to engage the slide member when the outer tube is in its extended position and the plunger is in its extended position and to move the outer tube from its extended position to its first retracted position in response to movement of the plunger from its first extended position to its retracted position, a stop member having a first position limiting the trigger handle from moving the plunger toward its second, extended position, and a second position permitting the trigger handle to move the plunger to its second, extended position.

13. The handle assembly of claim 12 wherein the drive tool further comprises an intermediate tube located between the outer tube and the plunger, the handle assembly further comprising a support to which the intermediate tube is mounted, the support being arranged to limit movement of the plunger beyond its second, extended position.

14. A drive tool assembly for delivering a suture securing device to a surgical site, the suture securing device including a first member and a second member configured for secure engagement with the first member, the drive tool assembly comprising:

an outer tube, the first member and the second member being located within the outer tube, a plunger located within the outer tube, a plunger actuator configured to move the plunger between a retracted position and an extended position, in the extended position, the plunger moving the second member into secure engagement with the first member, an outer tube actuator configured to move the outer tube between an extended position and a retracted position, and a coupler coupling the plunger and the outer tube, the coupler being configured to move the outer tube from its extended position to its retracted position in response to movement of the plunger from its extended position to its retracted position.

15. The drive tool assembly of claim 14 wherein the plunger actuator is configured to move the plunger to a second, further extended position, in the second, further extended position, the plunger deploys the secured first and second members from the drive tool assembly.

16. The drive tool assembly of claim 14 wherein the suture securing device includes a cartridge containing the first and second members, the drive tool assembly further comprising an intermediate tube located between the outer tube and the plunger for securing the cartridge to the drive tool.

17. The drive tool assembly of claim 16 wherein the outer tube actuator is configured to move the outer tube to a second, further retracted position, the intermediate tube being configured to engage and disengage the cartridge when the outer tube is in its second, further retracted position.

18. A method of delivering a surgical device, the surgical device including a first member and a second member, the method comprising:

providing a drive tool assembly including an outer tube, a plunger located within the outer tube, a plunger actuator configured to move the plunger, and a coupler coupling the plunger and the outer tube, moving the plunger actuator to partially advance the plunger to move one of the members into secure engagement with the other member, movement of the plunger actuator causing the coupler to engage the outer tube, and releasing the plunger actuator to move the plunger proximally, the coupler and the outer tube engaged by the coupler moving proximally in response to the proximal motion of the plunger.

19. The method of claim 18 further comprising moving the plunger actuator a second time to fully advance the plunger to eject the surgical device from the drive tool assembly.

20. The method of claim 18 further comprising moving an outer tube actuator to move the outer tube further proximally.

* * * * *